(12) United States Patent
Kam et al.

(10) Patent No.: US 11,185,404 B2
(45) Date of Patent: Nov. 30, 2021

(54) TENODESIS ANCHOR

(71) Applicant: CONMED CORPORATION, Utica, NY (US)

(72) Inventors: Andrew Kam, Odessa, FL (US); Peter Verdonk, Zwijnaarde (BE); Timothy Spalding, Leamington Spa (GB)

(73) Assignee: CONMED CORPORATION

( * ) Notice: Subject to any disclaimer, the term of this patent is extended or adjusted under 35 U.S.C. 154(b) by 210 days.

(21) Appl. No.: 16/297,793

(22) Filed: Mar. 11, 2019

(65) Prior Publication Data

US 2019/0274815 A1    Sep. 12, 2019

Related U.S. Application Data

(60) Provisional application No. 62/640,888, filed on Mar. 9, 2018.

(51) Int. Cl.
*A61F 2/08* (2006.01)

(52) U.S. Cl.
CPC .......... *A61F 2/0811* (2013.01); *A61F 2/0805* (2013.01); *A61F 2002/0829* (2013.01); *A61F 2002/0852* (2013.01); *A61F 2002/0882* (2013.01)

(58) Field of Classification Search
CPC combination set(s) only.
See application file for complete search history.

(56) References Cited

U.S. PATENT DOCUMENTS

| | | | |
|---|---|---|---|
| 9,173,652 B2 | 11/2015 | Lombardo et al. | |
| 9,826,971 B2 | 11/2017 | Lombardo et al. | |
| 2015/0173739 A1* | 6/2015 | Rodriguez | A61B 17/0401 606/232 |
| 2016/0157852 A1* | 6/2016 | Dougherty | A61B 17/0401 606/232 |

* cited by examiner

*Primary Examiner* — Yashita Sharma
(74) *Attorney, Agent, or Firm* — Bond, Schoeneck & King, PLLC; Frederick J. M. Price

(57) ABSTRACT

A tenodesis anchor having an anchor member coupled to at least one fiber loop. The anchor member is inserted into a bone and the loop closed about a tendon to be anchored to the bone. Closing the loops additionally deforms the anchor member so that it remains within the bone, thereby securing the tendon trapped in the loop to the bone without the use of a staple.

5 Claims, 6 Drawing Sheets

TENODESIS ANCHOR

CROSS-REFERENCE TO RELATED APPLICATIONS

The present application claims priority to U.S. Provisional Application No. 62/640,888 filed on Mar. 9, 2018.

BACKGROUND OF THE INVENTION

1. Field of the Invention

The present invention to tenodesis anchors and, more specifically, to a soft anchor and loop system for securing a tendon to bone without staples.

2. Description of the Related Art

The treatment of tendonitis, such as biceps tendonitis, may require a surgical procedure to repair a torn tendon and reattach it to the appropriate bone. This procedure is known as tenodesis and involved cutting the attachment of the tendon to the bone, removing any torn portion, then reattaching the tendon to the bone. Reattachment of the tendon to the bone is typically performed using staples. Staples can be irritating to the patient, however, as they are rigid and are typically used in series so that they occupy a large footprint. Accordingly, there is a need in the art for an approach for anchoring the tendon to bone in a tenodesis procedure that is less irritating and preferably avoids the use of staples.

BRIEF SUMMARY OF THE INVENTION

The present invention comprises a tenodesis anchor system for attaching a tendon to bone without the use of staples. The tenodesis anchor system comprise an anchor member having a series of slots formed therein and at least one closable loop that is woven through the series of slots in the anchor member and has a predetermined diameter for accepting a tendon therein. The loop includes a free end that, when pulled, will reduce the diameter of the loop and cause the loop to slide relative to the anchor member to capture the tendon therein. The anchor member is configurable between a first configuration that will pass through a hole in a bone and a second configuration that cannot pass through the hole in response to sliding of the loop relative to the anchor member. In one embodiment, two loops pass through the series of slots in the anchor member. A first end of each of the loops is fixed and second end of each of loops forms the free ends that, when pulled, will reduce the diameter of each of the loops. The system may further comprise an inserter extending along a longitudinal axis and having a first end configured as a fork having a pair of spaced apart tines. The pair of tines are configured to form a hole in a bone when driven therein.

The present invention also comprises a method of attaching a tendon to bone. The first step is providing an anchor member having a series of slots formed therein and at least one loop having a predetermined diameter that is woven through the series of slots in the anchor member and terminates in a free end that, when pulled, will cause the loop to slide relative to the anchor member. Next, the anchor member into a bone so that the loop remains on the outside of the bone. A tendon may then be passed through the loop and the free end of the loop pulled to reduce the diameter of the loop until the tendon is securely trapped within the loop.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1:
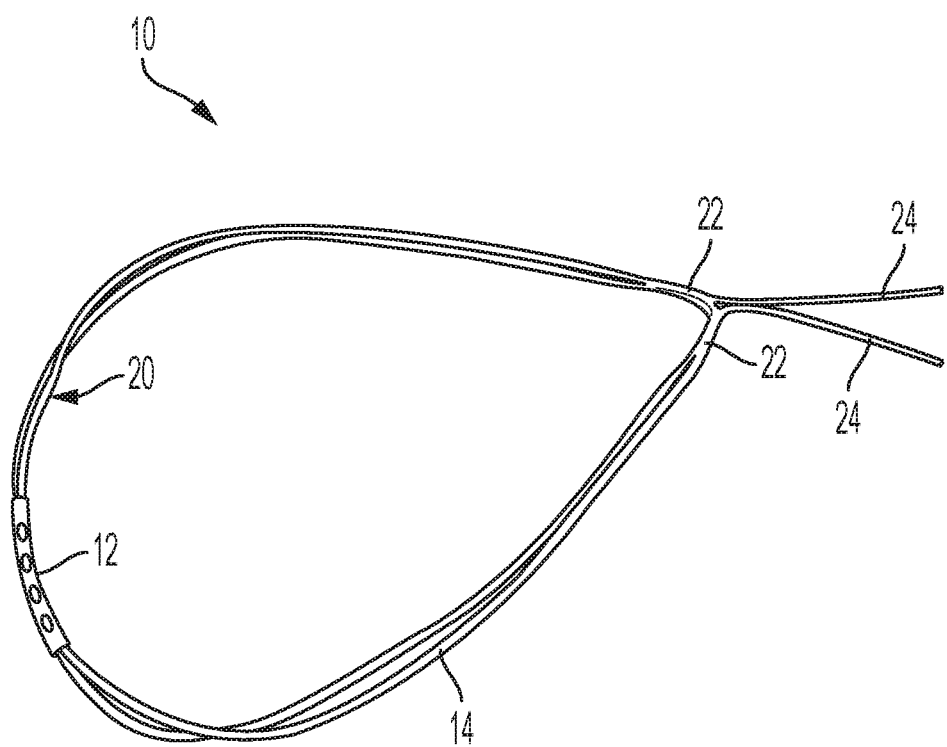
FIG. 1 is a schematic of a tenodesis anchor system according to the present invention.
Figure 2:
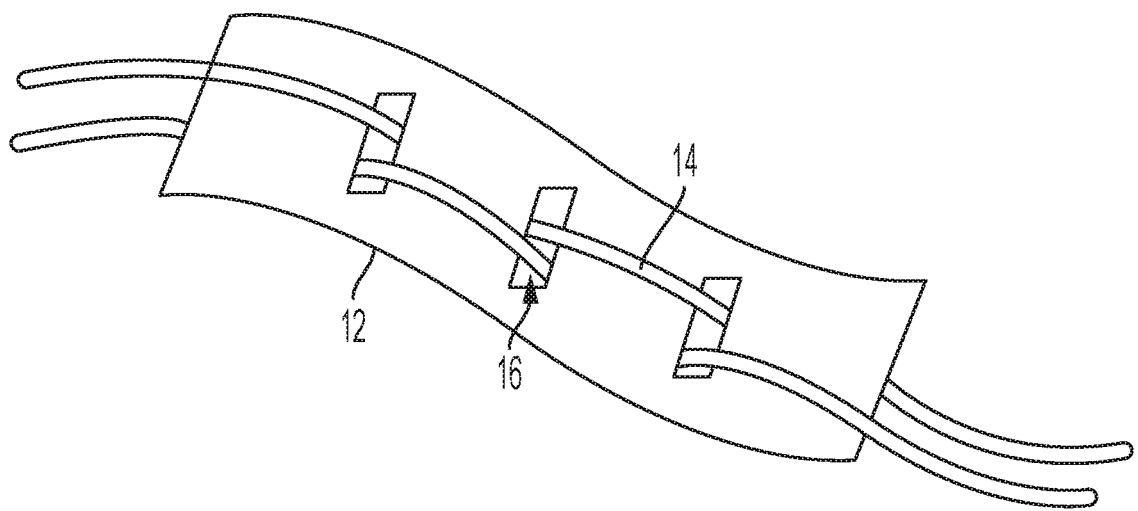
FIG. 2 is a schematic of an anchor member for a tenodesis anchor system according to the present invention.

Referring to the figures, wherein like numeral refer to like parts throughout, there is seen in FIG. 1 a tenodesis anchor 10 according to the present invention. Anchor 10 comprises an anchor member 12 spliced to a fiber 14, such as by weaving fiber 14 through a series of slots 16 formed in anchor member 12, as seen in FIG. 2. Anchor member 12 preferably comprises a fibrous pad that will be compressed into a different shape as a result of movement of fiber through anchor member 12 when anchor member is held in place within a bone. Alternatively, anchor member 12 may comprise a rigid anchor formed from metal plastic or a bioabsorbable material through which fiber 14 may slide.

Figure 3:
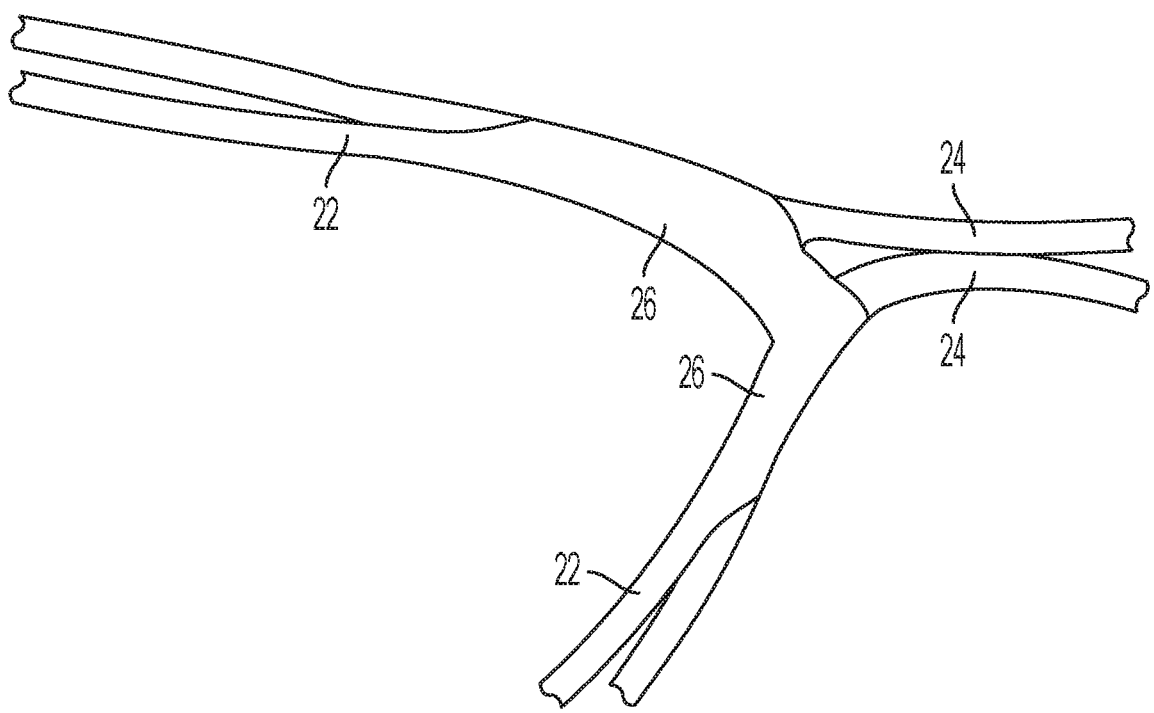
FIG. 3 is a schematic of a pair of loops that are interconnected according to the present invention

Fiber 14 may be configured as multiple loops 20 each of which have a predetermined diameter and each of which passes through slots 16. Loops 20 each have a fixed end 22 that is fixed to the other loop 20 and a free end 24 that can slide relative to the other loop 20. For example, as seen in FIG. 3, fixed end 22 of loop 20 may be configured to form a tube 26 through which free end 24 of the other loop 20 can freely pass, and vice versa. It should be recognized that various approaches may be used for securing fixed ends 22 and allowing for movement of free ends 24, such as running knots, eye splices, sliding splices, etc. As each loop 20 can slide freely through anchor member 12 independently of each other, a force applied to free end 24 of each loop 20 will cause loops 20 to reduce in diameter as free ends 24 slide though or relative to the fixed ends 22 of the other loop 20.

Figure 4:
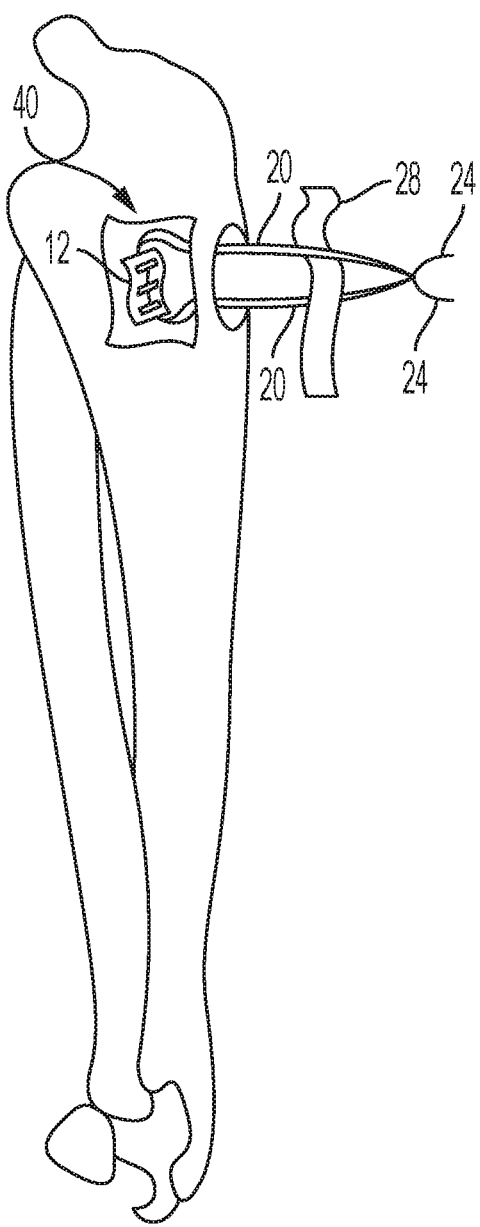
FIG. 4 is a schematic of an inserter for a tenodesis anchor according to the present invention.

Referring to FIG. 4, anchor member 12 may be inserted through a small aperture 40 formed into a bone with loops 20 remaining on the outside of the bone. A tendon 28 may be positioned within loops 20 and free ends 18 pulled to reduce the diameter of loops 20. When free ends 18 are pulled so that loops 20 are substantially closed, tendon 28 will become trapped in loops 20 and anchor member 12, if formed from a fibrous pad, will become compressed into a configuration that cannot slide out of bone aperture 40. Consequently, tendon 28 will be secured within loops 20 and anchor member 12 will hold loops 20, and thus tendon 28, securely in place against the bone. Thus, tendon 28 to be anchored in place may be placed through loops 20 and free ends 24 pulled to close loops 20 around tendon 28 and also compressing anchor member 12 into a configuration that cannot be withdrawn from the insertion hole. The ends of loops 20 may then be tied up to prevent loops 20 from opening.

Figure 5:
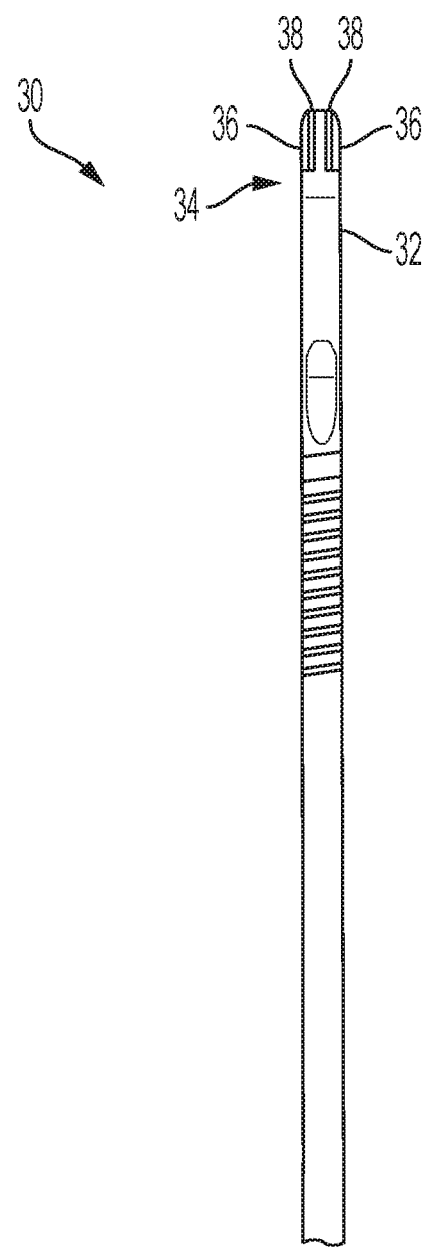
FIG. 5 is a schematic of an inserter coupled to a tenodesis anchor according to the present invention prior to inserting the anchor into a bone.

Referring to FIG. 5, the present invention also includes an inserter 30 adapted for installation of anchor 10 in a bone. Inserter 30 extends along a longitudinal axis to an end 32 defining a fork 34 having a pair of tines 36 that terminate in sharp points 38.

Figure 6:
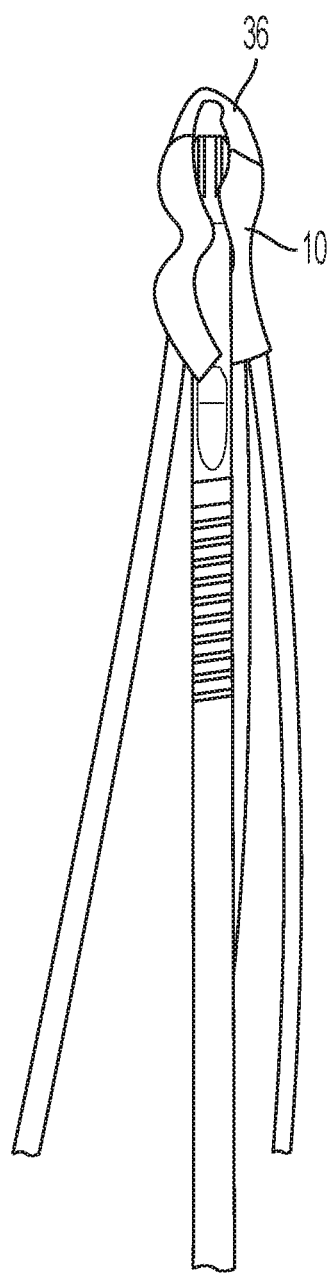
FIG. 6 is a schematic of a tenodesis anchor according to the present invention installed into a bone and ready to secure a tendon in place.

Referring to FIG. 6, anchor 10 may be positioned between tines 36 and inserter 30 mechanically driven longitudinally into a bone so that sharp points 38 form an insertion hole therein and anchor member 20 is pushed into the bone through the insertion hole. Withdrawal of inserter 30 will leave anchor member 20 within the bone.

What is claimed is:

1. A tenodesis anchor system, comprising:
   an anchor member having a series of slots formed therein; and
   at least two loops each of which is woven through the same series of slots in the anchor member and has a predetermined diameter for accepting a tendon therein, wherein each loop includes a fixed end and a free end such that pulling of the free end will reduce the diameter of the loop and cause the loop to slide relative to the anchor member.

2. The tenodesis anchor system of claim 1, wherein the anchor member is configurable between a first configuration that passes through a hole in a bone and a second configuration that cannot pass through the hole in response to sliding of the loop relative to the anchor member.

3. The tenodesis anchor system of claim 1, wherein the free ends of each of the two loops pass through the fixed ends of the two loops.

4. The tenodesis anchor system of claim 3, further comprising an inserter extending along a longitudinal axis and having a first end configured as a fork having a pair of spaced apart tines.

5. The tenodesis anchor system of claim 3, wherein the pair of tines are configured to form a hole in a bone when driven therein.

* * * * *